United States Patent [19]

Reinstein et al.

[11] Patent Number: 5,369,454
[45] Date of Patent: Nov. 29, 1994

[54] SYSTEM AND METHOD FOR PRODUCING AND MAINTAINING PARALLEL AND VERTICAL FIXATION OF VISUAL AXIS

[75] Inventors: Dan Z. Reinstein, New York; Ronald H. Silverman, Brooklyn, both of N.Y.; Donald J. Coleman, Haworth, N.J.

[73] Assignee: Cornell Research Foundation, Inc., Ithaca, N.Y.

[21] Appl. No.: 146,214

[22] Filed: Nov. 1, 1993

[51] Int. Cl.⁵ .......................... A61B 3/02; A61B 8/10
[52] U.S. Cl. .................................. 351/201; 351/204; 351/243; 351/246; 128/661.06
[58] Field of Search .................. 606/4, 5; 128/661.06, 128/745; 351/200, 201, 204, 208, 222, 237, 239, 243, 246

[56] References Cited

U.S. PATENT DOCUMENTS

| | | | |
|---|---|---|---|
| 1,327,163 | 1/1920 | Mathewson et al. | 351/204 |
| 2,197,139 | 4/1940 | Warner | 33/200 |
| 2,361,534 | 10/1944 | Eppenstein | 351/204 |
| 2,477,518 | 7/1949 | Kappauf et al. | 351/204 |
| 2,596,264 | 5/1952 | Macbeth | 33/200 |
| 3,371,660 | 3/1968 | Carlin | 138/661.06 |
| 4,057,054 | 11/1977 | Giannone | 351/203 |
| 4,368,958 | 1/1983 | Buget | 351/204 |
| 4,653,881 | 3/1987 | Joncour | 351/204 |
| 4,838,676 | 6/1989 | Buget et al. | 351/202 |
| 4,958,932 | 9/1990 | Kegelman et al. | 356/383 |

Primary Examiner—Anita Pellman Gross
Assistant Examiner—David R. Parsons
Attorney, Agent, or Firm—Perman & Green

[57] ABSTRACT

An apparatus for assuring vertical alignment of visual axes of a patient's eyes includes an eye cup that enables establishment of a liquid bath in which a surface of a cornea of a supine patient's first eye is completely submerged. A first light source is positioned above the liquid bath and directs a beam of alignment light to the submerged eye. A second light source is positioned above the patient's second eye and directs a beam of adjustment light to its corneal surface. Apparatus is provided that enables relative movement between the first and second light sources so as to enable the light sources to be moved into a position where the patient indicates a fusion of the light sources into a single spot, at which point it is known that the visual axis are vertical and aligned. The liquid bath assures that the beam of alignment light from the first light source is only in focus at the patient's eye when the first light source is directly coincident with the vertical axis of the first eye. Any deviation from that vertical axis results in blurring of the image due to refractive effects within the liquid bath.

6 Claims, 2 Drawing Sheets

SYSTEM AND METHOD FOR PRODUCING AND MAINTAINING PARALLEL AND VERTICAL FIXATION OF VISUAL AXIS

FIELD OF THE INVENTION

This invention relates to a system and method for producing standardized and reproducible positioning of the eye in space by assuring vertical and parallel fixation of a patient's visual axes, and more particularly, to such a system that may be used in conjunction with an ultrasound imaging system.

BACKGROUND OF THE INVENTION

Surgical alteration of the shape of a patient's cornea to improve visual acuity has been practiced for a number of years. Such surgery, termed "radial keratotomy", involves the making of radial cuts into the surface of the cornea so as to alter its external curvature. More recently, excimer lasers have been employed to ablate sections of a patient's cornea to modify its optical properties (termed "laser keratectomy"). Such laser-based surgery may be preceded by ultrasonic imaging of both the patient's corneal surface and a measurement of thickness variations of the cornea across its surface. Knowledge of thickness variations of individual corneal layers enables the surgeon to apply proper levels of laser power during the surgical procedure.

Refractive corneal surgery depends on accurate corneal shape alterations performed relative to the visual axis. In using ultrasound analysis (or any other system) to determine corneal micro-anatomy and shape, it is preferable that the ultrasound image be centered relative to the visual axis. In this way, the imaging study and the corneal surgical procedure will be similarly aligned, and pre- or post-operative studies can be reliably correlated. Applicants' system is intended to produce alignment of the visual axis to the vertical, and thus produce exactly the same positioning of the eye (relative to the earth) whether pre-, intra- or post-operative. The prior art has attempted to accomplish alignment of visual axes by asking the patient, while in a supine position, to focus on a light spot projected on the ceiling. Due to the relative closeness of the projected light spot, this procedure results in patient's visual axes always being somewhat convergent.

The prior art includes a number of different systems for both measuring inter-pupillary distance and for localizing the position of the visual axes of the eyes for placement of spectacle lenses. Such apparatus may be found in the following patents: 1,327,163 of Mathewson et al; 2,197,139 of Warner; 2,361,534 of Eppenstein; 2,477,518 of Kappauf et al; 2,596,264 of Macbeth; 4,057,054 of Giannone; 4,653,881 of Joncour and 4,838,676 of Buget et al. Each of the noted patents describes apparatus which must be placed in front of the eye and would obscure the eye (and its internal structures) from an ultrasound scanner.

Accordingly, it is an object of this invention to provide an apparatus and method for assuring parallel and vertical alignment and fixation of a patient's visual axes so as to enable standardization of the position of the visual axis for ultrasonography and laser treatment of the eye while the visual axes are in a known position.

It is another object of this invention to provide an improved method for assuring vertical and parallel alignment of visual axes of a patient's eyes, wherein convergence or divergence is avoided.

SUMMARY OF THE INVENTION

An apparatus for assuring alignment of visual axes of a patient's eyes includes an eye cup that enables establishment of a liquid bath in which a surface of a cornea of a supine patient's first eye is completely submerged. A first light source is positioned above the liquid bath and directs a beam of alignment light to the submerged eye. A second light source is positioned above the patient's second eye and directs a beam of adjustment light to its corneal surface. Apparatus is provided that enables relative movement between the first and second light sources so as to enable the light sources to be moved into a position where the patient indicates a fusion of the light sources into a single spot, at which point it is known that the visual axis are vertical and aligned. The liquid bath assures that the beam of alignment light from the first light source is only in focus at the patient's eye when the first light source is directly coincident with the vertical axis of the first eye. Any deviation from the vertical visual axis results in blurring of the image due to refractive effects within the liquid bath.

DETAILED DESCRIPTION OF THE INVENTION

Figure 1:
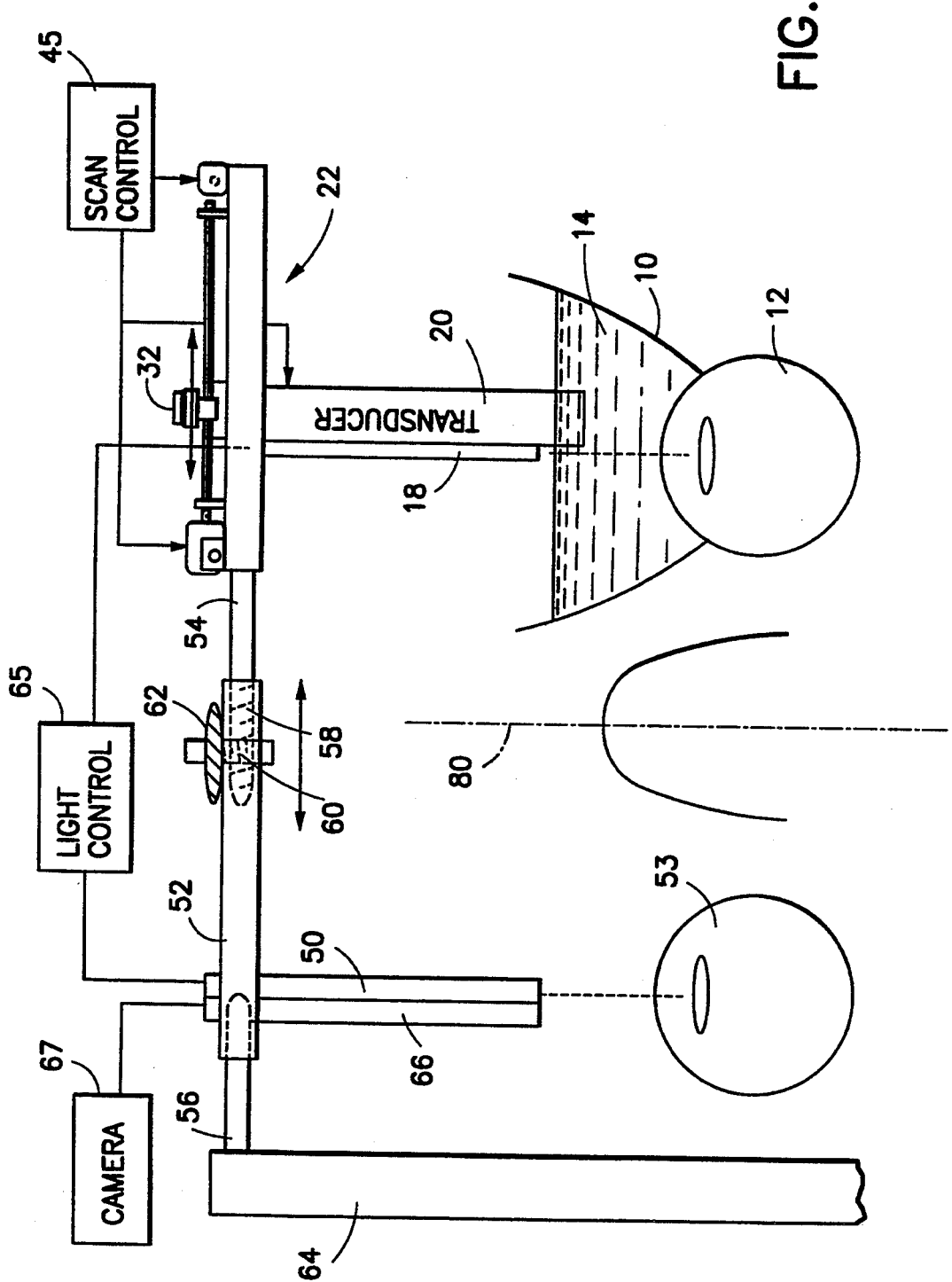
FIG. 1 is a schematic view of apparatus that incorporates the invention.

Referring to FIG. 1, an eye cup 10 is positioned against a patient's eye 12 to be examined so as to provide a sealed container for a liquid bath 14 (e.g. a normal saline solution). The distal opening of eye cup 10 bears upon the sclera of eye 12 and provides a bottom seal to prevent escape of liquid bath 14. A light fiber 18 is mounted vertically over eye 12 and is rigidly attached to an ultrasound transducer 20. The distal end of ultrasound transducer 20 is immersed in liquid bath 14 so as to be able to interrogate structures within eye 12 (including the corneal surface) and to measure corneal layer thicknesses.

Figure 2:
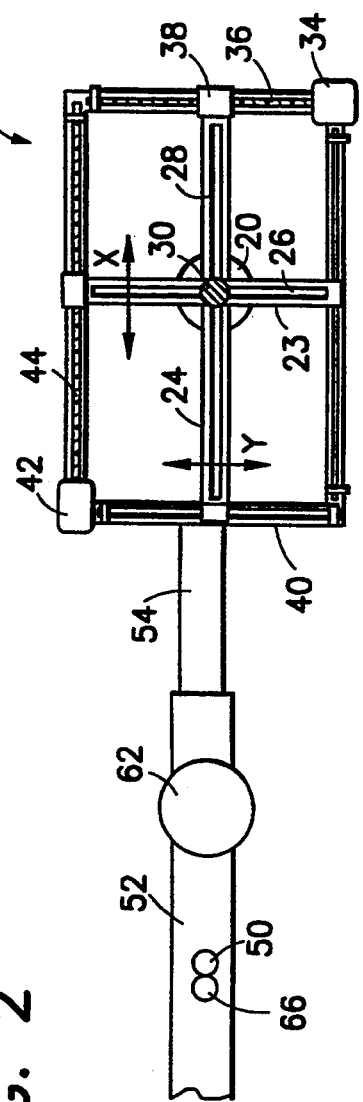
FIG. 2 is a schematic plan view of a portion of the apparatus of FIG. 1.

Both light fiber 18 and ultra sound transducer 20 are mounted on X-Y positioning mechanism 22. A top view of an exemplary X-Y positioning mechanism 22 is shown in FIG. 2. A pair of movable struts 23 and 24 enable movement of ultrasound transducer 20 and light fiber 18 in either the X or Y direction shown by the respective horizontal and vertical arrows in FIG. 2. Each of struts 23 and 24 includes a through-slot (i.e. 26, 28) through which a post 30 extends from ultrasound transducer 20. A cap 32 (see FIG. 1) is rigidly attached to the uppermost portion of post 30 and rides upon outer rails that border slot 26 in strut 23. A motor 34 operates a worm gear 36 which in turn, impels a follower gear 38 that is rigidly attached to strut 24. At the opposite extremity of strut 24, is a track 40 which supports strut 24. By control of the direction of rotation of motor 34 strut 24 can be moved in the Y direction within X-Y positioning mechanism 22. A similar motor 42 operates a helical gear 44 that controls the X position of strut 23. Concurrent operation of motors 34 and 42 by a scan control module 45 enables both ultrasound transducer 20 and light fiber 18 to be moved anywhere within mechanism 22 (and transducer 20 activated to scan eye 12).

A second light fiber 50 is rigidly attached to a hollow strut 52 that is mounted for travel on a pair of arms 54 and 56. Arm 54 is rigidly attached to mechanism 22 and is threaded at its end 58 to engage a worm gear 60. A knob 62 enables actuation of worm gear 60. Arm 56 is attached to vertical post 64. Rotation of knob 62 in either a clockwise or counterclockwise direction enables light fibers 18 and 50 to either move towards each other or away from each other. Light is provided to light fibers 18 and 50 from light control 65.

A further fiber 66 is mounted co-linearly with light fiber 50 and is connected to a camera 67 to enable video tracking of the position of the pupil within eye 52.

Figure 3B:
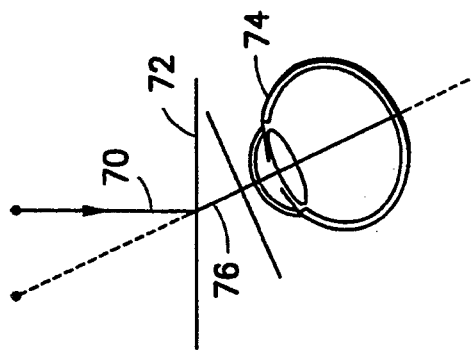
FIGS. 3A and 3B illustrate sections of the eye beneath the liquid bath, and enable a fuller understanding of the invention.
Figure 3A:
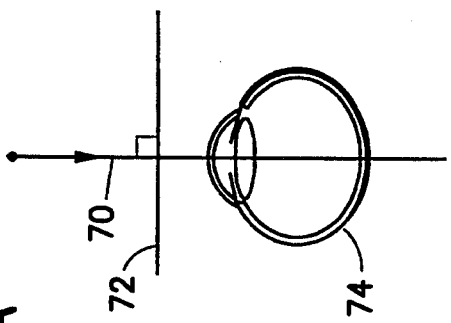

Prior to discussing the operation of the system of FIG. 1, reference should be made to FIGS. 3A and 3B. Light experiences refraction as it passes from one medium to another due to its differential speed of propagation in each medium. However, as is shown in FIG. 3A, a light beam 70 entering a liquid medium 72 experiences no refraction so long as its angle of incidence is perpendicular to the surface of liquid medium 72. Thus, if light beam 70 is not only perpendicular to the surface of liquid medium 72, but is also aligned with the visual axes of eye 74, the patient will see a well focused spot, notwithstanding the intervention of liquid medium 72. By contrast (see FIG. 3B), if light beam 70 is not perpendicular above the visual axis of eye 74, the result is that eye 74 focuses on a refracted beam 76. Under these conditions, liquid medium 72 causes an exaggerated displacement of the visual axis of eye 74 (due to refractive action of liquid medium 72). Further, the spot seen by the patient appears diffuse and be un-focused. In essence, liquid bath 72 magnifies any non-verticality between light beam 70 and the visual axis of eye 74.

The provision of a liquid medium over one of a patient's eyes prevents the phenomenon of fusion from occurring, except when light fibers 18 and 50 are directly over and vertically aligned with the optical axes of eyes 12 and 52 (FIG. 1). Fusion occurs when two point light sources appear as one to the patient, as a result of fusion of two retinal images by the brain. This only occurs when light beams from light fibers 18 and 50 are vertically above eyes 12 and 52 and are aligned with their respective visual axes. In such case, the angle of incidence of the light beam from light fiber 18 is perpendicular to the surface of liquid medium 14. Since the surface of liquid medium 14 is always perfectly horizontal, it is assured, upon a patient reporting fusion of light beams from light fibers 18 and 50, that the patient's visual axes are both parallel and vertical.

In operation, light sources (not shown) for light fibers 18 and 50 are initially switched on. The distance between light fibers 18 and 50 is initially set greater than the interpupillary distance and approximately equidistant from the supine patient's midline 80. The patient is then asked to look into the distance and upwardly. Then, knob 62 is operated to bring light fibers 18 and 50 towards each other and the patient is asked to report when the two light points are seen as one. The distance between light fibers 18 and 50 may then be increased, after a report of fusion, to adjust for a maximum distance that still produces fusion of the two light points. This ensures that "fusion" of the two light points from light fibers 18 and 50 occur without convergence. At this point, the patient's visual axes are parallel and vertical. Verticality is assured because eye 12 is submerged in liquid medium 14 and therefore must have its visual axis normal to the surface of liquid medium 14 for the light spot from fiber 18 to be in focus and to fuse with the light from fiber 50.

At this point, the light source that feeds fiber 18 is turned off and the patient continues to fix on the light from fiber 50, without convergence. The patient still reports a single light spot. Ultrasound transducer 20 is now energized and imaging commences, i.e. transducer 20 is free to image the cornea of eye 12 in parallel, consecutive scans.

To correct for possible movement of a patient's visual axes during scanning, the positioning of the pupil of eye 52 is image-tracked by video imaging of the cornea of eye 52 through fiber 66. This tracking information is used to enable accurate topographic mapping of the images made of the cornea of eye 12 (due to the fact that the eye movements are yoked together).

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. Apparatus for assuring vertical and parallel alignment of visual axes of a patients first and second eyes, the patient being in a generally supine position and having a liquid bath established about said first eye wherein said first eye is completely submerged in the liquid bath, said apparatus comprising:

first light source means positioned above said liquid bath, for directing a beam of alignment light to said patient's first eye;

second light source means positioned above said patient's second eye for directing a beam of alignment light to said second eye; and means for enabling relative movement between said first and second light sources so as to move said first and second light sources into a position where said patient indicates a fusion of said beams of said alignment light into a single spot.

2. The apparatus as recited in claim 1, further comprising:

an ultrasonic transducer positioned in contact with said liquid bath and rigidly attached to said first light source means; and means for terminating said beam of alignment light from said first light source means when said patient reports fusion and for commencing operation of said ultrasonic transducer.

3. The apparatus as recited in claim 2 wherein said first and second light source means comprise light fibers that produce beams of alignment light directed to said first and second eyes.

4. The apparatus as recited in claim 3, further comprising means for moving said ultrasonic transducer and first light source in an X-Y plane, said X-Y plane orthogonally oriented with respect to said beam of alignment light from said first light source means.

5. A method for assuring vertical and parallel alignment of visual axes of a patient's first and second eyes, said method comprising the steps of:

establishing a liquid bath about a patient's said first eye such that said first eye is completely submerged in said liquid bath;

positioning a light source above said liquid bath so that a beam of alignment light is directed to said patient's first eye;

positioning a second light source above said patient's second eye for directing a beam of alignment light to said second eye; and providing relative movement between said first and second light sources to move said beams of alignment light to a point where both beams of alignment light are visualized by said patient and said patient reports a fusion of said beams of alignment light into a single beam.

6. The method as recited in 5 further comprising the steps of:

terminating said beam of alignment light from said first light source when said patient reports a fusion; and operating an ultrasonic transducer to interrogate said first eye.

* * * * *